United States Patent

Rybák et al.

[11] Patent Number: 5,118,614
[45] Date of Patent: Jun. 2, 1992

[54] CONCENTRATES OF COAGULATION FACTORS II, VII, IX AND X, METHOD OF THEIR PREPARATION AND USE

[75] Inventors: Miroslav Rybák; Evzen Kasafírek, both of Prague; Jitka Houskova, Letovice; Cyril Losticky, Prague; Stanislav Ulrych, Prague; Oldrich Sedlmaier, Prague; Alena Roubalová, Prague, all of Czechoslovakia

[73] Assignee: Tessek sdruzeni Praha, Prague, Czechoslovakia

[21] Appl. No.: 297,753

[22] Filed: Jan. 17, 1989

[30] Foreign Application Priority Data

Jan. 18, 1988 [CS] Czechoslovakia ............... 324-88
Feb. 12, 1988 [CS] Czechoslovakia ............... 869-88
Apr. 28, 1988 [CS] Czechoslovakia ............... 2890-88

[51] Int. Cl.$^5$ .......................................... C12Q 1/56
[52] U.S. Cl. ................................ 435/13; 530/383; 530/384
[58] Field of Search ............. 435/13, 4; 530/384, 530/383

[56] References Cited

U.S. PATENT DOCUMENTS 4,160,025  7/1979  Eibl et al. ................... 424/101

Primary Examiner—Christine Nucker
Assistant Examiner—Jeffrey Stucker
Attorney, Agent, or Firm—Leydig, Voit & Mayer

[57] ABSTRACT

The claimed invention concerns concentrates of coagulation factors II, VII, IX and X and the method of their preparation by selective adsorption on an equilibrated carrier of hydroxyethylmethacrylate or hydroxyethylacrylate with bound diethylaminoethyl groups, followed by selective elution.

The concentrates of coagulation factors II and X can be used to detect coagulation factor VII and in a laboratory method for the detection or determination of the extent of mammalian inflammatory diseases.

14 Claims, No Drawings

CONCENTRATES OF COAGULATION FACTORS II, VII, IX AND X, METHOD OF THEIR PREPARATION AND USE

FIELD OF THE INVENTION

The invention relates to concentrates of coagulation factors from human and animal blood plasma or fractions thereof, the so-called "prothrombin complex," a group of coagulation factors dependent on vitamin K and known as factors II, VII, IX and X, and the method of their preparation and use.

BACKGROUND OF THE INVENTION

Coagulation factors, in the form of more or less pure concentrates, represent an important material for the preparation of parenteral compositions for clinical use and laboratory diagnosis of coagulation disorders and for use as markers of certain disease. The preparations are used by patients with a hereditary or acquired deficiency in blood coagulation, by acute hemorrhagy, pre-surgery prophylaxis of bleeding, damage of liver parenchyme, or by vitamin K deficiency; etc.

The established method for preparation of these coagulation factor concentrates, using sorbents based on a polysaccharide matrix, e.g., diethylaminoethyl- or DEAE-, has some disadvantages. The polysaccharide matrix is highly susceptible to microbial contamination, which causes physical and chemical changes in the sorbent. Polysaccharide sorbent particles are less resistant to change in environmental conditions, e.g., temperature, pressure, salt concentration, etc., the result of which is a change in the sorbent's volume with all the undesirable resulting consequences. Because of the different matrix of the hydroxyalkyl methacrylate sorbent, on the one hand, and polysaccharide, on the other hand, the behavior of the coagulation factors, i.e., factor II, VII, IX and X, during chromatographic separation on these materials is different to a certain degree.

BRIEF SUMMARY OF THE INVENTION

Sorbents based on a synthetic matrix of DEAE-hydroxyethylmethacrylate or DEAE-hydroxyethylacrylate particles, which are established, commercially obtainable, preparations, e.g., Separon HEMA DEAE (Tessek, Praque), used in the method according to the invention, do not have the above-described disadvantages of polysaccharide sorbents. The synthetic matrix is resistant to microbial contamination and does not change its quality during changes in physical and chemical conditions. The sorbents are very stable and can be used for a long time without changes in adsorption properties. In certain cases it may be useful to add proteinase inhibitors (benzamidine) for the blocking of autoactivation. The separation can be done by column chromatography or by using the batch method. The choice of sorbent particle size depends on the technology of separation. The advantageous physical and chemical properties of these sorbents improve the possibility of a complex fractionation of blood plasma to the required products. The resistance of sorbents against high pressure makes possible rapid and standard workcycles with a possibility of precise production of individual steps of the technology and automation of the separation process. The character of the carrier enables liquids to flow under pressure, keeping the time limits of technological operations and improving their course. If the coagulation factors are prepared as more or less purified concentrates, they may be, after stabilization, pasteurized to inactivate viruses.

The concentrates of coagulation factors II and X, prepared according to the invention, can be used for the detection and diagnosis of human and animal inflammatory diseases. Functionally pure coagulation factors VII, II and X are extensively used in diagnosis. The concentrates of factors II and X can be used to improve the quantitative determination of factor VII and some other factors in blood plasma and body fluids. The control of identity of the separated factors can be made with functional, i.e. coagulation, enzyme and immunochemical tests.

DETAILED DESCRIPTION OF THE INVENTION

We claim the invention of concentrates of coagulation factors II, VII, IX and X, prepared by bringing the biological material that contains the above-mentioned factors into contact with a sorbent based on DEAE-hydroxyethyl methacrylate polymer followed by elution with a buffer of pH 7.2–7.6 and saline concentration 0.3–2.0M.

These concentrates of coagulation factors from human or animal blood plasma or from their fractions are prepared in such a manner that the starting raw material is brought into contact with the DEAE-hydroxyethyl methacrylate polymer carrier sorbent equilibrated with buffer, pH 7.2–7.6, that contains 0.1M saline. After the adsorption of coagulation factors, unabsorbed proteins are washed away with the same buffer containing 0.2M saline. Then the elution of a protein fraction, either functionally pure or a mixture, of factors II, VII, IX and X follows. The elution is achieved with a saline gradient of 0.3–2.0M in the starting buffer. It is advantageous to use citrate buffer, pH 7.2–7.6, that contains 0.01M trisodium citrate and sodium chloride as saline.

A concentrate of coagulation factor IX is obtained by elution with the above-mentioned buffer containing 0.3–0.4M saline. A concentrate of coagulation factors II and X is obtained by elution with a buffer containing 0.45–0.55M saline. A concentrate of coagulation factor VII is eluted with buffer containing 0.7–0.8M saline.

It is known that inflammation in a mammalian organ is accompanied by increased permeability of the blood vessel walls, due in part to the action of peptides called kinins. With the increased permeability of the blood vessel walls, both corpuscular and protein blood components appear in the body fluids. Some indirect detection methods of uro-genital and glandula lactica inflammation, e.g., detection of proteins and leukocytes in urine, detection of albumin, alpha$_1$-antitrypsin and the so-called somatic cells in milk, are based on the results of increased blood vessel permeability. These methods have some limits from the point of sensitivity and laboratory technology. The importance of early diagnosis of inflammatory diseases is widely accepted. Mastitis, i.e., inflammation of the glandula lactica, which occurs in cattle, is an important barrier to constant high production and quality of milk. The later the illness is ascertained in the animal, the more difficult, longer and more expensive is the necessary treatment. The possibility of early, specific, sensitive and simple detection of mastitis incidence, mostly under the conditions of intensive husbandry, is very important. A high concentration of plasma proteins in milk also appears, under physiological conditions, during and up to the 20th day after delivery. When destabilization of vessel walls appears in milk-producing organs in a time not related to this period, it is always a signal of pathological processes. Quantitatively, the rate of protein penetration is proportional to the extent of mastitis. Qualitatively, proteins with a low molecular mass penetrate more easily. Detection of mastitis on the basis of the determination of serum albumin or alpha$_1$-antitrypsin in milk has been published (Sandholm M. et al , J. Dairy Res. 51: 1–9 (1984)). Albumin is difficult to detect by chromogenic tests. Alpha-antitrypsin can be detected using chromogenic substrates and trypsin but the process has certain methodological problems.

The authors of the claimed invention demonstrated that plasma procoagulant, coagulation factor VII, appears very early in the course of kidney and glandula lactica inflammation in urine and milk, respectively, and, on the basis of this observation, succeeded in the development of a method useful for the detection of inflammation of mammalian organs and the determination of its extent without the need for any pre-treatment of the respective body fluids. The method may be generally used in all cases when body fluids, including diagnostic lavages, come into contact with the afflicted organ. The invention deals also with the method of detection or determination of the extent of inflammatory disease, using techniques of body-fluid analysis in human urine and in animals, especially bovine milk. The methods are based on the fact that a sample of the investigated body fluid comes either in one or two steps into contact with a solution, containing thromboplastin, phospholipids and $Ca^{2+}$ ions, and another solution, containing a concentrate of coagulation factors II and X. Afterwards, the liberated thrombin is detected with a chromogenic substrate and the intensity of the resulting color may be, if it is necessary, determined quantitatively, e.g., by comparison with a standard or by using instrumental technology, e.g., spectrophotometry.

The origin of the claimed invention lies in the finding of the authors that the plasma procoagulant, i.e., coagulation factor VII, is one of the first plasma proteins that penetrates from the blood flow into the body fluids, such as urine and milk, during organ inflammation. The concentration of this procoagulant in the body fluid is in direct proportion to the intensity of the ongoing inflammation and its size. Factor VII, together with tissue thromboplastin, $Ca^{2+}$ ions and phospholipids initiates the so-called extrinsic pathway of blood coagulation activation:

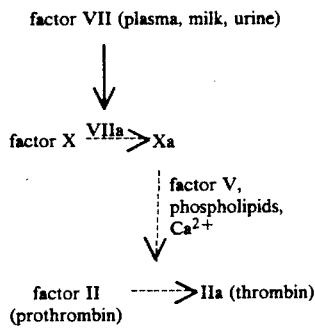

Factor VII is activated by the action of a reagent (reagent 1), which contains tissue thromboplastin, $Ca^{2+}$ and phospholipids to factor VIIa. In milk, $Ca^{2+}$ and phospholipids evidently participate in this activation. Upon single or stepwise addition of the reagent (reagent 2) containing a concentrate of factors II and X, factor X is gradually activated to factor Xa. Together with a cofactor, factor V, which is partially present in "reagent 2" and also partially present in body fluids of animals with a disequilibrated system of organ vessel walls, it changes factor II to factor IIa (thrombin), i.e., the proteinase, which, under certain conditions, splits suitable chromogenic peptide substrates. Their cleavage products have an expressive and characteristic color on which may be based a sensitive detection method and, with the help of useful devices, a quantitative determination:

thrombin + Z—Gly—Pro—Arg—X ⟶ (A)

Z—Gly—Pro—Arg—OH +p-nitroaniline

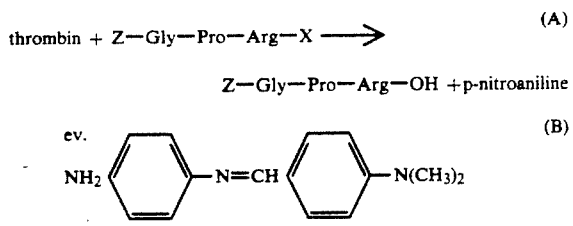

X is p-nitroaniline (A) or a N, N-bis derivative of p-phenylene diamine bound by a azomethine bound with an aldehyde chromophore, e.g., 4-dimethylaminobenzaldehyde (B) or 4-dimethylaminocinnamaldehyde. Z is benzyloxycarbonyl.

Use of the factor II and X concentrate makes the method according to the claimed invention highly sensitive. Values obtained from the instruments used for the determination or gained by comparison with a color standard give information about the extent of the disease. It may be said that the level of factor VII is minimal in body fluids of healthy subjects and high in subjects with organ inflammation. From a quantitative point of view, the level of factor VII is in good relation with the clinical state of the patient and, due to the high sensitivity of the test, a subclinical state of illness may be detected by this method, too. An alternative for using concentrate of factor X is the use of a synthetic substrate for factor Xa, eliminating the use of concentrates of factor II and X, but the sensitivity of this alternative does not reach the sensitivity for determination of factor VII through prothrombin/thrombin conversion. When the necessary instrumentation, namely autoanalyzers, is available, it is possible to perform spectrophotometric, quantitative analysis of a large number of samples. A second alternative, using diagnostic devices, for example diagnostics strips, is suitable for a quick semiquantitative test without great demand on laboratory (instrumental) technique and personnel qualifications.

Peptide derivatives of the general structure Z-Gly-Pro-Arg-X, where the X and Z are as mentioned above, may be used a suitable chromogenic substrates in methods according to the claimed invention. The chromophore (X) is chosen according to the method of determination or instrumental equipment or according to the fact, if the detection is done in solution, or using a suitable diagnostic device (dry chemistry) on the basis of inert organic or inorganic materials, which are generally known from laboratory practice. It is possible to use substrates of another type, of course, only in the event that they have suitable qualities.

The method according to the claimed invention is highly sensitive and specific. Mastitis may be diagnosed with its help before the onset of clinical symptoms so it is possible to begin the prophylactic treatment earlier. Duration of the disease is shorter and chances for a quick recovery are greater. This way it is possible to prevent great economic losses. The most simple, practical way of doing the test, which is the subject of the claimed invention, involves putting a sample of milk in sodium citrate (3.8%, 1+9) and, after transport to a laboratory, which has the necessary equipment, analyzing the milk immediately. The samples may be sorted below $-10°$ C. and, after an accumulation of a number of samples, jointly analyzed after thawing. Milk samples also may be removed by means of absorptive material, such as paper. The sample is dried and analyzed after elution. The latter method of sample preparation enables easy transport of the samples into a central laboratory, even from distant localities. The sample is then extracted for a certain time and, at the same time, activated with "reagent 1". The subsequent procedures are the same as for analysis of native milk. Using this method, casein, the lipid components and cellular elements stay on the absorption material and the eluate, containing factor VII, is a clear liquid.

The invention is described more clearly by way of the following examples. These examples illustrate the claimed invention but do not limit its use.

EXAMPLE 1

Preparation of Concentration of Coagulation Factors II, VII, IX and X

Normal human plasma (native fresh plasma) or the so-called K-plasma (plasma free of cryoprecipitate) with a controlled pH 7.2–7.6 is used as a source of the coagulation factors. One liter of plasma is brought into contact with DEAE-hydroxyethylmethacrylate gel in a column (100–150 ml) equilibrated with a starting buffer, pH 7.4, of 0.01M trisodium citrate containing 0.1M sodium chloride. The size of the sorbent particles is 80–100 $\mu$m. After the adsorption of coagulation factors, unadsorbed and weakly bound proteins are removed by washing with the starting buffer containing 0.2M sodium chloride. The elution of all other proteins that remain bound after washing is done with increasing concentrations of saline in the starting buffer up to 2.0M. All factors of the "prothrombin complex," i.e., factor II, VII, IX, X and protein C, are localized in the resulting eluate. The fraction is then processed to a solution suitable for substitution therapy. Using a sorbent containing 1.2–1.3 mval/g of DEAE-groups and a particle size of 80–100 $\mu$m, it is possible to purify 60–90% of the "prothrombin complex" components from normal human plasma using the described procedure. These proteins represent the main protein component of the obtained concentrate.

Regeneration of the sorbent is performed by an intensive washing of the sorbent with citrate buffer, containing 2.0M sodium chloride, followed by distilled water and starting buffer for the next cycle of use.

EXAMPLE 2

Preparation of Concentration of Factors IX and X, besides Factors IX and VII

One liter of human plasma is passed through a column of DEAE-hydroxyethylmethacrylate under the same conditions as in Example 1. After removal of balast proteins by citrate buffer, pH 7.4, containing 0.2M saline, elution is achieved with a salt gradient from 0.2 to 0.8M saline in the starting buffer, pH 7.4. Adsorbency of the eluted proteins was measured with the help of a photometer at 280 nm. The fraction containing factor IX was eluted from the column at saline concentration 0.3–0.4M. At a saline concentration of 0.45–0.55M, a solution containing factor II and X was eluted from the column. At a concentration of saline of 0.7–0.8M, a portion containing functionally pure factor VII was eluted from the column. For some purposes it is suitable to pool the fraction containing factor IX and the fraction containing II and X into a single preparation. At a saline concentration of 0.5M, a fraction containing factors IX, II and X was obtained. After the NaCl concentration was increased to 0.8M, a fraction containing factor VII was eluted. In all cases, the process takes place in the starting buffer, pH 7.4. The obtained concentrate of factor VII is free from other factors of the "prothrombin complex" and the concentrate of factors IX, II and X is free from factor VII. The quantitative ratios are similar to those in Example 1.

EXAMPLE 3

Preparation of Prothrombin Concentrate (factor II) from the Washing Solution (0.4M sodium acetate, pH 7.4) Obtained by the Separation of Plasma Antithrombin III The fraction obtained by the separation of antithrombin III on a heparin-hydroxyethylmethacrylate sorbent contains, in addition to a little amount of factor IX, X and protein C, a considerable portion of prothrombin, which can be separated by the method according to the claimed invention.

One liter of the washing solution is diluted with distilled water to a two-fold volume and filtrated through a column of DEAE-hydroxyethylmethacrylate, which was equilibrated with 0.2M sodium acetate at pH 7.4. After adsorption and washing of the column with 0.2M acetate (0.2 mol/l), elution was achieved with saline in buffer in the same way as in Example 1.

EXAMPLE 4

Preparation of Prothrombin Concentrate from Ethanol Fraction III

Ethanol fraction III, obtained during fractionation of human blood plasma, is used as a raw material for the preparation of prothrombin. 100 g of this fraction, in the form of wet precipitate, are suspended in 1 liter of 0.01M citrate buffer, pH 7.4, with 0.1M saline. After 2 hours of mixing at 0°–4° C., the suspension is centrifuged and the supernatant, after eventual filtration, is processed in the same way as the plasma in Examples 1 and 2.

EXAMPLE 5

Preparation of "Prothrombin Complex" Coagulation Factors from Bovine Plasma

The separation is performed according to Example 2 with the exception that bovine blood plasma is used as the source of coagulation factor concentrates. The separated concentrate of factor II and X is used as a reagent for the identification and determination of factor VII in milk, which enables detection of bovine mastitis.

EXAMPLE 6a

Determination of Coagulation Factor VII in Cattle Milk

A sample of milk (0.1–10 μl) is mixed with 200 μl of reagent 1+2, the preparation of which is shown below, and incubated for either 5 min at 37° C. or 10 min at 25° C. Then the substrate, e.g., 0.3M Z-Gly-Pro-Arg-p-nitroanilide, is added to the mixture and the rate of hydrolysis is determined with the spectrophotometer as the amount of hydrolyzed p-nitroaniline ($\Delta A_{405}$/min). The activity of thrombin and the concentration of factor VII in the milk can be determined based on the amount of hydrolyzed p-nitroaniline.

Reagent 1+2

5 ml of concentrate of factor II and X in 0.05M Tris buffer, pH 8.2, are mixed with 5 mls of the solution of thromboplastin, refrigerated below −40° C., stored and used after thawing. Lyophilised concentrate of factor II and X may be also mixed with lyophilised thromboplastin, homogenized and tableted. Using reagent 1+2, a sample of milk is diluted 1+100 with Tris buffer, pH 8.2, containing 5 mM $CaCl_2$.

EXAMPLE 6b

A sample of milk (0.1–10 μl) is mixed with 200 μl of reagent 1 and 50 μl of reagent 2 (the preparation of which is shown below) and incubated for either 5 min at 37° C. or 10 min at 25° C. Afterwards, substrate is added to the mixture and the mixture is then processed as in Example 6a.

Reagent 1

2 ml 0.05M Tris buffer, pH 8.2, containing 5 mM calcium chloride is mixed with 0.5 ml thromboplastin solution in such a concentration that 200 μl of the resulting mixture activate the amount of factor VII present in 1 μl of normal human or bovine plasma. For the determination of factor VII in 0.1–10 μl milk, 200 μl of the above-mentioned reagent was used.

Reagent 2

Concentrate of factor II and X is dissolved in 0.05M Tris buffer, pH 8.2, and used for the determination of factor VII in 0.1–10 μl of milk in such a volume as to contain about 10–12 nkat of factor II and 1–2 nkat of factor X per ml. The reagent must be devoid of factor VII.

Example 7

The same procedure was used as in Example 6b with the exception that the sample of milk was absorbed into a material with a high absorptive capacity, such as paper, and dried. Factor VII was extracted before the analysis for 20–60 min, with simultaneous activation by reagent 1. The clear, activated eluant was analyzed with the help of reagent 2. The area of a 20 mm² paper was extracted with 200–400 μl of the solution of reagent 1. The composition of reagent 1 and 2 is the same as in Example 6b.

EXAMPLE 8

A defined volume of milk or pre-diluted milk was put in a small bottle, containing reagent 1 in a suitable form (tableted, lyophilised), in such an amount that would complete activation of factor VII present in the milk in 10 min at 25° C. After this time, but no longer than 1 hour, a diagnostic strip, containing reagent 2, buffer, pH 8.2, substrate (e.g., Z-Gly-Pro-Arg-NH-C₆H₄-N=CH—C₆H₄—N(CH₃)₂ and chromophore/arylaldehyde, e.g., 4-dimethylaminocinnamaldehyde, 50 μl 2 mM solution per 1 cm²) was dipped into the reagent mixture. The hydrolysis product of thrombin produces an intensive blue-colored substance after acidification/-reaction with chromophore. The intensity of the color is in direct proportion to the quantity of factor VII in the milk. Evaluation is made either semiquantitatively, by comparison with a colored standard, or quantitatively, by the measurement of the intensity of the color with a reflexphotometer. The composition of reagent 1 and 2 is the same as in Example 6b.

EXAMPLE 9

The same procedure was used as in Example 8, except the strip contains reagent 1+2 in addition to the substrate, buffer, chromophore and acidification-reagent. The composition is the same as that in Example 6a.

EXAMPLE 10

The same procedure was used as in Examples 6, 8 and 9 except that human urine or another body fluid, essentially the solution used for washing of the afflicted organ, was used as the sample. In healthy subjects the amount of factor VII in urine is minimal. An increase is a sign of an inflammatory process of the urogenital tract, essentially the organ where the lavage was made.

What is claimed is:

1. A concentrate of a coagulation factor selected from the group consisting of coagulation factors II, VII, IX and X, wherein the coagulation factor is prepared by contacting a biological material selected from the group consisting of human blood plasma, animal blood plasma and fractions thereof, containing one or more of the above mentioned factors, with a sorbent based upon a synthetic matrix selected from the group consisting of polymers of diethylaminoethyl-hydroxyethylacrylate, polymers of diethylaminoethyl-hydroxyethylmethacrylate, and mixtures thereof, and desorbing the desired coagulation factor by eluting the sorbent with a buffered solvent having a pH from 7.2–7.6 and a saline content of 0.3–2.0 mol/l.

2. A method for detecting the presence of factor VII in a fluid comprising contacting said fluid with concentrates of coagulation factors II and X in the presence of thromboplastin, phospholipids, $Ca^{2+}$-ions and a chromogenic substrate, and observing whether a color change occurs, indicating the presence of factor VII.

3. The method of claim 2 wherein the fluid employed is derived from a mammal and the method of detecting the presence of factor VII is used for the detection or determination of the extent of inflammatory disease in said mammal.

4. The method of claim 2 wherein the chromogenic substrate is a peptidic derivative of the following structure structure:

Z-Gly-Pro-Arg-X where X is a p-nitroaniline residue of an N,N'-bis derivative of p-phenylendiamine bound by an azomethine bond with a chromophoric aldehyde and Z is benzyloxycarbonyl.

5. A method of preparation of coagulation factor concentrates selected from the group consisting of coagulation factors II, VII, IX and X comprising contacting a human or animal blood plasma or a fraction thereof, wherein said fluid is contacted with a sorbent based upon a synthetic matrix selected from the group consisting of polymers of diethylaminoethyl-hydroxyethylacrylate, polymers of diethylaminoethyl-hydroxyethylmethacrylate, and mixtures thereof, equilibrated with a buffer with a pH of 7.2–7.6 and a saline concentration of 0.1 mol/l, removing the unbound proteins by washing with the same buffer containing 0.2 mol/l saline, and desorbing the desired coagulation factors with a buffer containing saline at a concentration from 0.3 to 2.0 mol/l.

6. The method according to claim 5 wherein citrate buffer is used as the buffer with a pH of 7.2–7.6 containing 0.01 mol/l trisodium citrate and 0.1 mol/l sodium chloride.

7. The method according to claim 5 wherein sodium acetate is used as the solution with a pH of 7.2–7.6.

8. The method according to claim 5 wherein the fluid is contacted with the sorbent by flow through a chromatographic column or by a batch method.

9. The method according to claim 5 wherein concentrate of coagulation factor IX is obtained by desorption with a buffer containing 0.3–0.4 mol/l saline.

10. The method according to claim 5 wherein concentrate of coagulation factors II and X is obtained by desorption with a buffer containing saline at a concentration of 0.45–0.55 mol/l.

11. The method according to claim 5 wherein coagulation factor VII is obtained by elution with a buffer containing saline at a concentration of 0.7–0.8 mol/l.

12. A method for determination of the presence of coagulation factor VII in a biological fluid for the determination of the extent of mammalian inflammatory disease by analysis of the body fluids wherein samples of said biological fluid are collected and then are simultaneously or in a stepwise manner brought into contact with thromboplastin, phospholipids, concentrate of coagulation factors II and X, $Ca^{2+}$-ions and a chromogenic substrate and evaluating the resulting color.

13. The method according to claim 12 wherein the chromogenic substrate is selected from the group consisting of peptide derivates of the general structure: Z-Gly-Pro-Arg-X, where X is a p-nitroaniline residue or an N,N'-bis derivative of p-phenylendiamine bound by an azomethine bond with a chromophoric aldehyde and Z is benzyloxycarbonyl.

14. The method of claim 13 wherein the chromogenic substrate is selected from the group consisting of 4-dimethylaminobenzaldehye or 4-deimethylaminocinnamaldehyde.

* * * * *